United States Patent
Goto et al.

(10) Patent No.: US 10,722,188 B2
(45) Date of Patent: Jul. 28, 2020

(54) X-RAY CT APPARATUS

(71) Applicant: CANON MEDICAL SYSTEMS CORPORATION, Otawara-shi (JP)

(72) Inventors: Takahiro Goto, Utsunomiya (JP); Shinsuke Tsukagoshi, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 15/983,840

(22) Filed: May 18, 2018

(65) Prior Publication Data

US 2018/0333110 A1 Nov. 22, 2018

(30) Foreign Application Priority Data

May 18, 2017 (JP) .................. 2017-099234
May 17, 2018 (JP) .................. 2018-095577

(51) Int. Cl.
| | | |
|---|---|---|
| A61B 6/03 | (2006.01) | |
| A61B 6/00 | (2006.01) | |
| A61B 6/02 | (2006.01) | |
| A61B 5/05 | (2006.01) | |
| A61B 6/04 | (2006.01) | |

(52) U.S. Cl.
CPC .............. *A61B 6/032* (2013.01); *A61B 5/05* (2013.01); *A61B 6/027* (2013.01); *A61B 6/405* (2013.01); *A61B 6/4476* (2013.01); *A61B 6/4482* (2013.01); *A61B 6/469* (2013.01); *A61B 6/488* (2013.01); *A61B 6/545* (2013.01); *A61B 6/04* (2013.01)

(58) Field of Classification Search
CPC ........... A61B 5/05; A61B 6/027; A61B 6/032; A61B 6/04; A61B 6/469
See application file for complete search history.

(56) References Cited

U.S. PATENT DOCUMENTS

| | | | |
|---|---|---|---|
| 6,212,251 B1 * | 4/2001 | Tomura ................. | A61B 6/032 378/15 |
| 6,233,308 B1 * | 4/2001 | Tomura ................. | A61B 6/032 378/15 |
| 7,257,190 B2 * | 8/2007 | Tsujii ..................... | A61B 6/032 378/19 |
| 2004/0008819 A1 | 1/2004 | Drummond et al. | |

(Continued)

FOREIGN PATENT DOCUMENTS

| | | |
|---|---|---|
| JP | 2004-33778 | 2/2004 |
| JP | 2005-40582 | 2/2005 |

(Continued)

*Primary Examiner* — Marcus H Taningco
(74) *Attorney, Agent, or Firm* — Oblon, McClelland, Maier & Neustadt, L.L.P.

(57) ABSTRACT

An X-ray CT apparatus comprises a gantry including an X-ray generator in a rotor, and processing circuitry configured to control rotation of the rotor during a first scan such that a value related to first rotational speed serving as rotational speed of the rotor at a time when the first scan is finished is brought close to a setting value related to second rotational speed serving as rotational speed of the rotor in a second scan, with respect to the first scan and the second scan performed after the first scan is performed.

19 Claims, 7 Drawing Sheets

(56) References Cited

U.S. PATENT DOCUMENTS

| | | | |
|---|---|---|---|
| 2004/0179644 A1* | 9/2004 | Tsuyuki | A61B 6/032 378/8 |
| 2005/0006586 A1* | 1/2005 | Balan | A61B 6/4429 250/363.02 |
| 2005/0008116 A1 | 1/2005 | Nishide et al. | |
| 2005/0074085 A1 | 4/2005 | Hsieh et al. | |
| 2007/0258558 A1 | 11/2007 | Nishide et al. | |
| 2008/0031407 A1 | 2/2008 | Satta et al. | |
| 2011/0081067 A1* | 4/2011 | Ye | A61B 6/032 382/131 |
| 2013/0279646 A1* | 10/2013 | Koike | G01N 23/046 378/15 |
| 2015/0092910 A1* | 4/2015 | Xing | A61B 6/032 378/8 |
| 2016/0220216 A1* | 8/2016 | Karahashi | A61B 6/54 |

FOREIGN PATENT DOCUMENTS

| | | |
|---|---|---|
| JP | 2005-111269 | 4/2005 |
| JP | 2007-229265 | 9/2007 |
| JP | 2007-289297 | 11/2007 |
| WO | WO 2010/047380 A1 | 4/2010 |

* cited by examiner

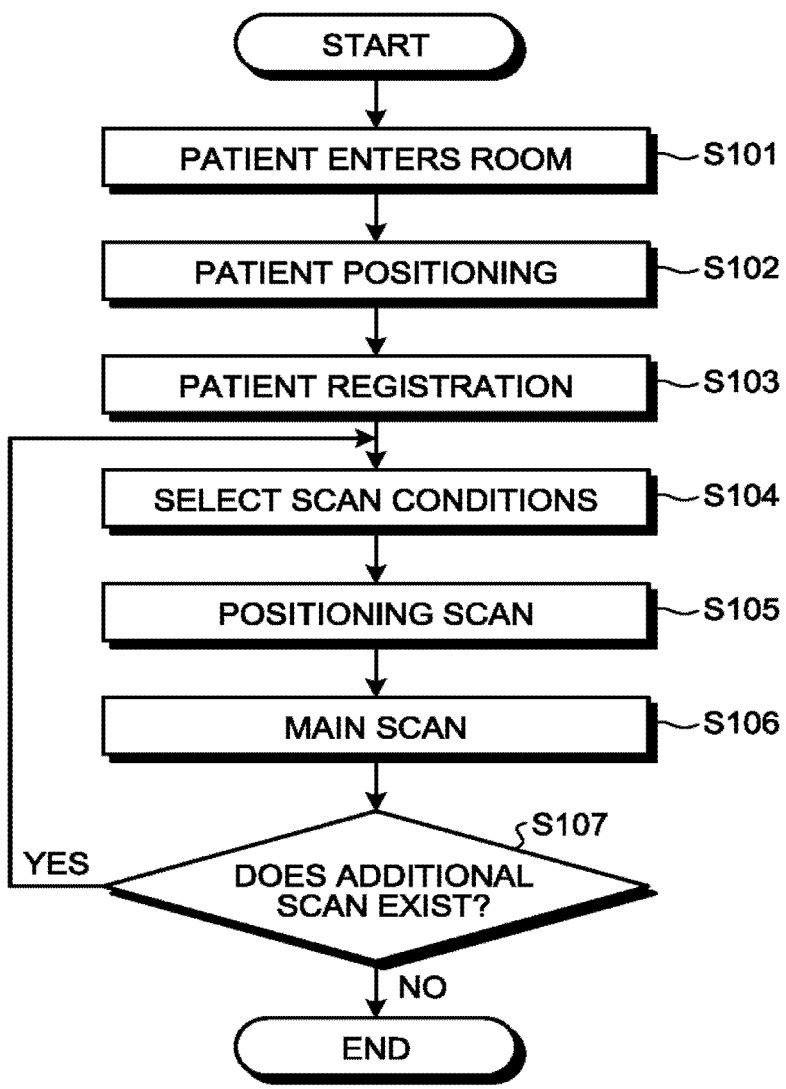

X-RAY CT APPARATUS

CROSS-REFERENCE TO RELATED APPLICATIONS

This application is based upon and claims the benefit of priority from Japanese Patent Application No. 2017-99234, filed on May 18, 2017; and Japanese Patent Application No. 2018-95577, filed on May 17, 2018, the entire contents of all of which are incorporated herein by reference.

FIELD

Embodiments described herein relate generally to an X-ray CT apparatus.

BACKGROUND

In inspection using an X-ray computed tomography (CT) apparatus, a positioning scan acquiring a positioning image (scanogram) is performed, in addition to a main scan acquiring a diagnostic image. For example, first, the X-ray CT apparatus performs a positioning scan in a state of stopping rotation of a rotor including an X-ray generator, or while rotating the rotor. Thereafter, the X-ray CT apparatus performs a main scan, with the rotor rotated at preset rotational speed for a main scan. In the case where a positioning scan is performed in a state in which rotation of the rotor is stopped, or in the case where the rotational speed of the rotor in a positioning scan is different from the rotational speed for a main scan, the main scan is not started until rotation of the rotor reaches the rotational speed for a main scan, and the operator and the subject are in a waiting state.

BRIEF DESCRIPTION OF THE DRAWINGS

FIG. 6 is a flowchart for explaining a flow of a process of the X-ray CT apparatus according to the first embodiment.

DETAILED DESCRIPTION

An X-ray CT apparatus comprises a gantry and processing circuitry. The gantry includes an X-ray generator in a rotor. The processing circuitry is configured to control rotation of the rotor during a first scan such that a value related to first rotational speed serving as rotational speed of the rotor at a time when the first scan is finished is brought close to a setting value related to second rotational speed serving as rotational speed of the rotor in a second scan, with respect to the first scan and the second scan performed after the first scan is performed.

The following is a detailed explanation of embodiments of the X-ray CT apparatus, with reference to drawings.

Figure 1:
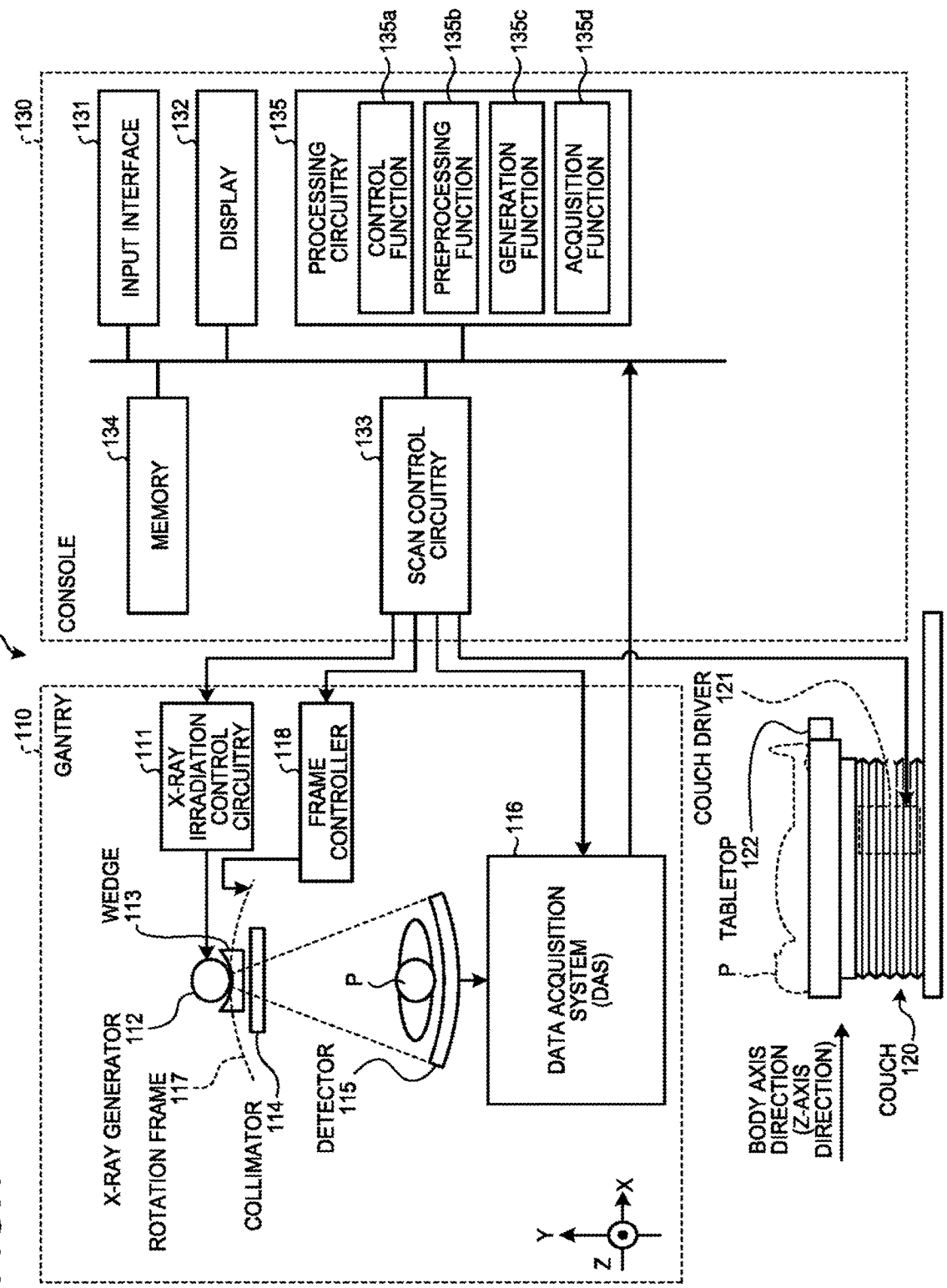
FIG. 1 is a block diagram illustrating an example of configuration of an X-ray CT apparatus according to a first embodiment.

First, the following is an explanation of an example of an X-ray CT apparatus according to a first embodiment, with reference to FIG. 1. FIG. 1 is a block diagram illustrating an example of an X-ray CT apparatus 100 according to the first embodiment. As illustrated in FIG. 1, the X-ray CT apparatus 100 according to the first embodiment includes a gantry 110, a couch 120, and a console 130.

The gantry 110 is an apparatus irradiating X-rays to a subject P, detecting the X-rays transmitted through the subject P, and outputting an electrical signal corresponding to the detected X-rays to the console 130. The gantry 110 includes an X-ray irradiation control circuitry 111, an X-ray generator 112, a wedge 113, a collimator 114, a detector 115, a data acquisition system (DAS) 116, a rotation frame 117, and a frame controller 118.

The rotation frame 117 is an annular frame supporting the X-ray generator 112, the wedge 113, the collimator 114, and the detector 115 such that the X-ray generator 112, the wedge 113, and the collimator 114 are opposed to the detector 115 with the subject P interposed therebetween. The rotation frame 117 is rotated at high speed with a circular track including the subject P serving as a center under a control of a frame controller 118.

The X-ray irradiation control circuitry 111 controls a high-voltage generator (not illustrated), to supply high voltage to the X-ray generator 112. The X-ray irradiation control circuitry 111 adjusts the tube voltage supplied to the X-ray generator 112 and/or a tube current in an X-ray tube comprising the X-ray generator 112, under the control of scan control circuitry 133, to adjust the X-ray quantity irradiated to the subject P. The X-ray irradiation control circuitry 111 also switches the wedge 113. The X-ray irradiation control circuitry 111 also adjusts the aperture of the collimator 114, to adjust the irradiation range (fan angle and/or cone angle) of the X-rays.

The X-ray generator 112 comprises, for example, an X-ray tube (vacuum tube) receiving supply of high voltage from an X-ray high-voltage device (not illustrated), and applying thermions from a cathode (also referred to as filament) to an anode (target), under the control of the X-ray irradiation control circuitry 111 (the X-ray generator 112 is an example of the X-ray generator). The X-ray generator 112 irradiates an X-ray beam to the subject P, with rotation of the rotation frame 117.

The wedge 113 is an X-ray filter to adjust the X-ray quantity of X-rays irradiated from the X-ray generator 112, under the control of the X-ray irradiation control circuitry 111. Specifically, the wedge 113 is a filter transmitting and attenuating X-rays irradiated from the X-ray generator 112 such that the X-rays irradiated from the X-ray generator 112 to the subject P has predetermined distribution. The wedge 113 is also referred to as wedge filter and/or bow-tie filter.

The collimator 114 is a slit to narrow down the irradiation range of the X-rays with the X-ray quantity adjusted with the wedge 113, under the control of the X-ray irradiation control circuitry 111. For example, the collimator 114 includes four slidable aperture blades. The collimator 114 slides the aperture blades, under the control of the X-ray irradiation control circuitry 111, to narrow down the X-rays generated with the X-ray generator 112 and irradiate the X-rays to the subject P. The aperture blades are plate-like members formed of lead or copper, and provided in the vicinity of the X-ray irradiation port of the X-ray generator 112, to adjust the irradiation range of the X-rays.

The detector 115 comprises, for example, a plurality of X-ray detection element lines, in each of which a plurality of X-ray detection elements are arranged in a channel direction along an arc, with the focus of the X-ray tube in the X-ray generator 112 serving as the center. The detector 115 has a structure in which a plurality of X-ray detection element lines, in each of which a plurality of X-ray detection elements are arranged in a channel direction, are arranged in a slice direction (Z-axis direction illustrated in FIG. 1). The detector 115 detects X-rays irradiated from the X-ray generator 112 and transmitted through the subject P, and outputs an electrical signal corresponding to the detected X-ray quantity to the data acquisition system 116. The detector 115 is, for example, an indirect-conversion detector formed of a grid, a scintillator array, and an optical sensor array. The scintillator array comprises a plurality of scintillators, and each of the scintillators is composed of a scintillator crystal outputting light of a photon quantity corresponding to the incident X-ray quantity. The grid is disposed on a surface on the X-ray incidence side of the scintillator array, and composed of an X-ray shield plate having a function of absorbing scattered X-rays. The optical sensor array has a function of converting light into an electrical signal corresponding to the light quantity from the scintillator, and is composed of an optical sensor, such as a photomultiplier tube. The X-ray detector may be a direct-conversion detector comprising a semiconductor device converting incident X-rays into an electrical signal (the detector 115 is an example of the X-ray detector).

The data acquisition system 116 is a DAS, and acquires CT projection data from detection data of X-rays detected with the detector 115. For example, the data acquisition system 116 comprises at least an amplifier performing amplification processing on the electrical signal output from each of the X-ray detection elements of the detector 115, and an A/D converter converting the electrical signal into a digital signal, and generates detection data (raw data). The detection data generated with the data acquisition system is transferred to the console 130 (the data acquisition system 116 is an example of the data acquirer). For example, the data acquisition system 116 performs amplification processing and/or A/D conversion on the X-ray intensity distribution data detected with the detector 115, to generate CT projection data, and transmits the generated CT projection data to the console 130. For example, when X-rays are continuously irradiated from the X-ray generator 112 during rotation of the rotation frame 117, the data acquisition system 116 acquires pieces of CT projection data for the whole circumference (360°). The data acquisition system 116 also associates each piece of acquired CT projection data with the tube position, and transmits them to the console 130. The tube position serves as information indicating the projection direction of the CT projection data.

The frame controller 118 rotates and drives the rotation frame 117, to rotate the X-ray generator 112, the wedge 113, and the collimator 114, and the detector 115 on a circular track with the subject P serving as the center. The frame controller 118 comprises processing circuitry and a drive mechanism. The processing circuitry in the frame controller 118 is, for example, a processor reading and executing a computer program from the memory 134, to achieve the functions. The drive mechanism includes, for example, a motor, and a mechanism (hereinafter also referred to as "actuator") converting the drive force from the motor. The frame controller 118 has a function of receiving an input signal from an input interface 131 (input device attached to the console 130 or the gantry 110), and controlling the operation of the gantry 110. For example, the frame controller 118 performs control to rotate the rotor, control to tilt the gantry 110, and operate the couch 120 and a tabletop 122, in response to an input signal (the frame controller 118 is an example of a frame controller).

In the following explanation, a part related to generation of X-rays irradiated to the subject P is also referred to as X-ray generator, in the configuration of the X-ray CT apparatus 100. For example, the X-ray generator includes the X-ray generator 112. The X-ray generator may also include the wedge 113 and/or the collimator 114, in addition to the X-ray generator 112. In the following explanation, a part related to detection of X-rays transmitted through the subject P is also referred to as X-ray detector, in the configuration of the X-ray CT apparatus 100. For example, the X-ray detector includes the detector 115. In the following explanation, a part rotatable in the gantry 110 is also referred to as rotor. In FIG. 1, the rotor includes the X-ray generator, the X-ray detector, and the rotation frame 117.

The couch 120 is a device on which the subject P is placed, and includes a couch driver 121 and a tabletop 122. The tabletop 122 is a plate on which the subject P is placed. The couch driver 121 moves the tabletop 122 in a Z-axis direction, to move the subject P into the rotation frame 117. For example, the couch driver 121 moves the tabletop 122, by converting the drive force from a motor (not illustrated) with an actuator.

Change in relative positions of the gantry 110 and the tabletop 122 may be achieved by controlling the tabletop 122, or by controlling traveling of the gantry 110 when the gantry 110 is of a self-movable type. In the following explanation, relative movement speed (speed of change in relative positions between the gantry 110 and the tabletop 122) of the gantry 110 and the tabletop 122 is also referred to as couch speed.

The console 130 is a device receiving operator's operations of the X-ray CT apparatus 100, controlling a scan in the gantry 110, and reconstructing CT image data (volume data) using CT projection data acquired with the gantry 110. As illustrated in FIG. 1, the console 130 includes an input interface 131, a display 132, the scan control circuitry 133, a memory 134, and processing circuitry 135.

The input interface 131 includes a mouse, a keyboard, a trackball, a switch, a button, a joystick, and/or a touch panel used by the operator of the X-ray CT apparatus 100 for inputting various instructions and/or various settings. The input interface 131 transfers information of the instructions and/or settings received from the operator to the processing circuitry 135.

The display 132 is a monitor referred to by the operator. The display 132 displays a positioning image and/or an X-ray CT image based on CT image data to the operator, under the control of the processing circuitry 135, and displays graphical user interface (GUI) to receive various instructions and/or various settings from the operator through the input interface 131.

The scan control circuitry 133 controls operations of the X-ray irradiation control circuitry 111, the frame controller 118, the data acquisition system 116, and the couch driver 121, to control processing of acquisition of CT projection data in the gantry 110, under the control of the processing circuitry 135. For example, the scan control circuitry 133 controls processing of acquisition of CT projection data, in a positioning scan to acquire a positioning image, and/or a main scan to acquire an X-ray CT image. The scan control circuitry 133 is capable of performing a positioning scan with the rotor of the gantry 110 rotated, and capable of performing a positioning scan with the rotor of the gantry 110 fixed. This point will be described later.

The memory 134 is, for example, a non-volatile storage device, such as a semiconductor memory device including a flash memory, a hard disk, and an optical disk. For example, the memory 134 stores CT projection data and/or CT image data therein. The memory 134 also stores therein setting values related to the rotational speeds of the rotor set for the respective inspected regions and purposes. For example, the memory 134 stores therein setting values related to the rotational speed of the rotor in the main scan in association with the regions of the subject P. The setting values related to the rotational speed of the rotor will be described later.

The processing circuitry 135 executes a control function 135a, a preprocessing function 135b, a generation function 135c, and an acquisition function 135d, to control the operation of the whole X-ray CT apparatus 100. For example, the processing circuitry 135 reads and executes a computer program corresponding to the control function 135a from the memory 134, to control the scan control circuitry 133 and control processing of acquisition of CT projection data in a positioning scan and/or a main scan. In addition, for example, the processing circuitry 135 reads and executes a computer program corresponding to the preprocessing function 135b from the memory 134, to subject the CT projection data to logarithmic transformation and correction, such as offset correction, sensitivity correction, and beam hardening correction, generate corrected CT projection data, and store the corrected CT projection data in the memory 134.

For example, the processing circuitry 135 also reads and executes a computer program corresponding to the generation function 135c from the memory 134, to reconstruct CT image data (volume data) using the CT projection data stored in the memory 134. Various methods exist as the reconstruction method, such as back projection. Examples of back projection include back projection using filtered back projection (FBP). As another example, the processing circuitry 135 may use iterative reconstruction (IR), to reconstruct CT image data. The processing circuitry 135 stores the reconstructed CT image data in the memory 134.

In addition, for example, the processing circuitry 135 reads and executes a program corresponding to the generation function 135c from the memory 134, to perform image generation processing on the CT image data stored in the memory 134, and generate a positioning image and/or an X-ray CT image. Specifically, the processing circuitry 135 generates a positioning image from CT image data based on CT projection data acquired by a positioning scan performed with the rotor of the gantry 110 rotated, and generates an X-ray CT image from CT image data based on CT projection data acquired by a main scan.

In the X-ray CT apparatus 100 illustrated in FIG. 1, each of the processing functions is stored in the memory 134, in the form of a computer program executable with a computer. The X-ray irradiation control circuitry 111, the scan control circuitry 133, and the processing circuitry 135 are processors reading and executing a computer program from the memory 134, to achieve the function corresponding to the computer program. In other words, the circuitry in a state of reading a computer program has a function corresponding to the read computer program.

FIG. 1 illustrates the structure in which the single processing circuitry 135 achieves the control function 135a, the preprocessing function 135b, the generation function 135c, and the acquisition function 135d, but a plurality of independent processors may be combined to form the processing circuitry 135, and the processors may execute the programs to achieve the functions.

The term "processor" used in the explanation described above means a central processing unit (CPU), a graphics processing unit (GPU), or a circuit, such as an application specific integrated circuit (ASIC) and a programmable logic device (such as a simple programmable logic device (SPLD), complex programmable logic device (CPLD), and a field programmable gate array (FPGA)). The processor achieves the function, by reading and executing a computer program stored in the memory 134. Instead of storing a computer program in the memory 134, the computer program may be directly incorporated in the circuit of the processor. In this case, the processor achieves the function, by reading and executing the computer program incorporated in the circuit thereof. Each of the processors according to according to is not limited to the case where each of the processors is formed as a single circuit, but a plurality of independent circuits may be combined as a processor, to achieve the function. In addition, a plurality of constituent elements in FIG. 1 may be integrated into a processor, to achieve the function.

In addition, the processing circuitry 135 may achieve the function using a processor of an external device connected through a network. For example, the processing circuitry 135 achieves the functions illustrated in FIG. 1, by reading and executing programs corresponding to the functions from the memory 134, and using an external workstation or a server group (cloud) connected with the X-ray CT apparatus 100 through a network, as calculation resources.

The configuration of the X-ray CT apparatus 100 has been described above. With the configuration, the X-ray CT apparatus 100 according to the present embodiment shortens the waiting time in inspection including a plurality of scans. Specifically, the X-ray CT apparatus 100 controls rotation of the rotor during a positioning scan such that the rotational speed of the rotor at the time when the positioning scan is finished is brought close to the rotational speed of a main scan, by processing with the processing circuitry 135 explained in detail below, to shorten the time required until the rotational speed reaches the setting value. The following is a detailed explanation of processing performed with the X-ray CT apparatus 100 according to the first embodiment.

First, the subject P enters the inspection room in which the X-ray CT apparatus 100 is positioned (the patient enters the room), the subject P is placed on the tabletop 122. Positioning of the subject P is performed in accordance with the irradiation range of X-rays (patient positioning). For example, from a projector included in the gantry 110, visible light indicating the irradiation range of X-rays is irradiated to a predetermined position in the longitudinal direction of the tabletop 122, with a predetermined width in the transverse direction of the tabletop 122, and positioning of the subject P is performed with reference to the irradiation position of the visible light. Thereafter, the control function 135a performs patient registration for the subject P. For example, the control function 135a receives input of the name, and a patient ID and the like of the subject P from the operator through the input interface 131, to perform patient registration.

Thereafter, the control function 135a sets scan conditions. The scan conditions are, for example, the tube voltage value and the tube current value in a main scan, the setting value related to the rotational speed of the rotor in a main scan, a field of view (FOV), the imaging slice thickness, the imaging range, and presence/absence of a positioning scan, and the like. In the case of performing a positioning scan, the scan conditions include selection as to whether the positioning scan is performed in the state in which the rotor is rotated, or the positioning scan is performed in the state in which the rotor is fixed. In the case of performing a positioning scan in the state in which the rotor is rotated, the scan conditions include the tube voltage value and the tube current value in the positioning scan, the setting value related to the rotational speed of the rotor in the positioning scan, the FOV, the imaging slice thickness, and the imaging range, and the like. Fixed conditions may be used as the scan conditions in the positioning scan. The following explanation illustrates the case where a positioning scan is performed.

As an example, the control function 135a displays combinations (expert plans) of preset conditions for the scan conditions to the operator, and receives an operation to select one of the displayed expert plans, to set the scan conditions. The expert plans may include reconstruction conditions, such as a reconstruction image thickness, a reconstruction interval, a reconstruction center, a start position and an end position of reconstruction, and a matrix size, in addition to the scan conditions.

Thereafter, the control function 135a controls the scan control circuitry 133, to control a positioning scan and acquire CT projection data from the subject P. For example, the control function 135a controls operations of the X-ray irradiation control circuitry 111, the data acquisition system 116, and the couch driver 121, to perform a positioning scan, in the state in which rotation of the rotor is stopped. As another example, the control function 135a controls the operation of the frame controller 118, in addition to the X-ray irradiation control circuitry 111, the data acquisition system 116, and the couch driver 121, to perform a positioning scan, while rotating the rotor.

In addition, the control function 135a controls operations of the X-ray irradiation control circuitry 111, the data acquisition system 116, the frame controller 118, and the couch driver 121, to perform a main scan, while rotating the rotor. The control function 135a is capable of performing a positioning scan performed with the rotor rotated and a main scan, by a helical scan or a non-helical scan. The following is an explanation of the case where a positioning scan and a main scan are performed by a helical scan, as an example.

Figure 2:
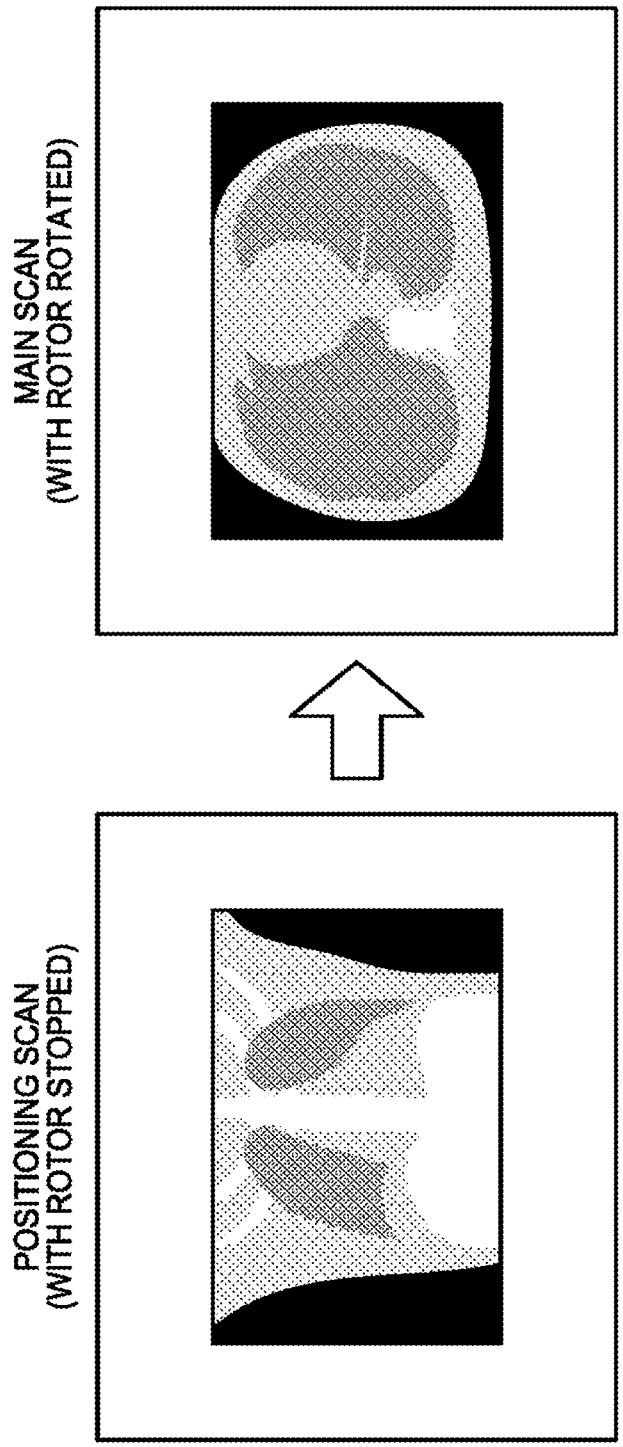
FIG. 2 is a diagram for explaining a positioning scan according to the first embodiment.

The following is an explanation of the case where a positioning scan is performed with the rotor of the gantry 110 fixed, with reference to FIG. 2. FIG. 2 is a diagram for explaining a positioning scan according to the first embodiment. In the case where a positioning scan is performed with the rotor of the gantry 110 fixed, the control function 135a moves the relative positions of the gantry 110 and the subject P placed on the couch 120, while X-rays are irradiated from the X-ray generator 112, to scan the whole body of the subject P along the body axis direction. By such a scan, for example, a two-dimensional image as illustrated in the left drawing of FIG. 2 is acquired as a positioning image.

Thereafter, the control function 135a sets the imaging range in a main scan on the basis of the positioning image illustrated in FIG. 2, and performs a main scan by a helical scan to scan the subject P in the set imaging range in a helical manner. In the case illustrated in FIG. 2, because the control function 135a has performed a positioning scan in the state in which the rotor of the gantry 110 is stopped, starting the main scan requires acceleration of rotation of the rotor of the gantry 110 to the setting value set for rotation of the main scan by selection of the expert plan or the like. The main scan is not started until rotation of the rotor reaches the setting value.

Figure 3:
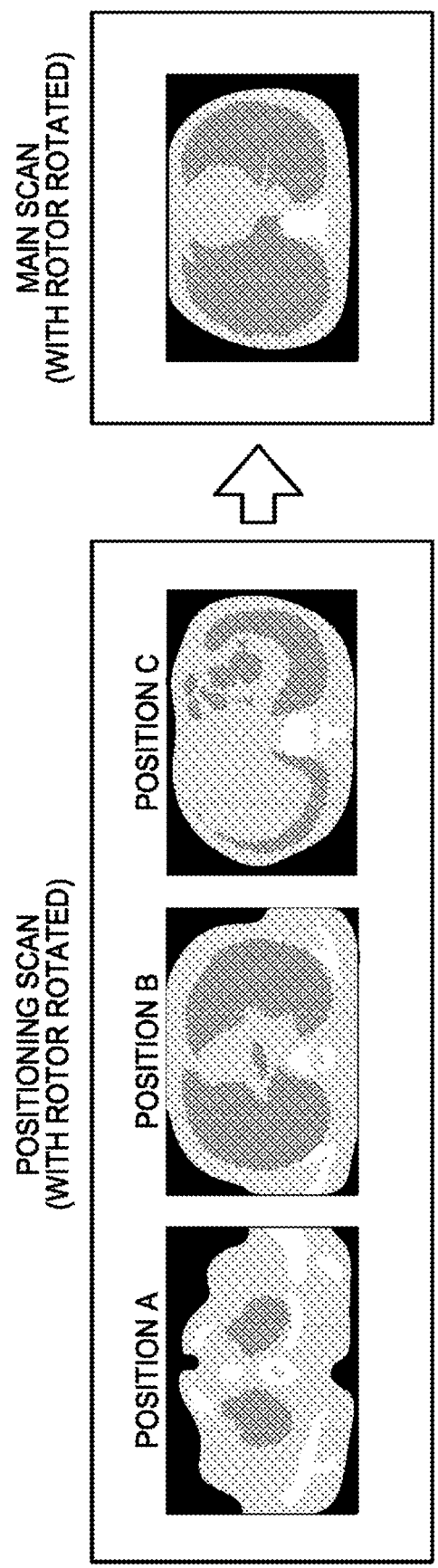
FIG. 3 is a diagram for explaining a positioning scan according to the first embodiment.

The following is an explanation of the case where a positioning scan is performed with the rotor of the gantry 110 rotated, with reference to FIG. 3. FIG. 3 is a diagram for explaining a positioning scan according to the first embodiment. In the case of performing a positioning scan with the rotor of the gantry 110 rotated, the control function 135a moves the relative positions of the gantry 110 and the subject P placed on the couch 120, while X-rays are irradiated from the X-ray generator 112 rotated and moving, to scan the whole body of the subject P along the body axis direction. A positioning scan performed while the rotor of the gantry 110 is rotated is an example of a first scan. For example, the control function 135a performs a positioning scan by a helical scan to scan the subject P in a helical manner.

After CT projection data is acquired by the positioning scan, the generation function 135c reconstructs CT image data using the CT projection data, and generates a positioning image from the reconstructed CT image data. The generated positioning image includes information of three-dimensional positional relation of the regions of the subject P. For example, the positioning image is generated as a cross-sectional image of the subject P. The left drawing in FIG. 3 illustrates a cross-sectional image at position A of the subject P, a cross-sectional image at position B of the subject P, and a cross-sectional image at position C of the subject P, as example of the positioning image generated with the generation function 135c.

The X-ray CT apparatus 100 is capable of performing a positioning scan by a helical scan, with an exposure dose approximately equal to that in the case of performing a positioning scan with the rotor fixed, by using a low dose imaging technique (such as an image reconstruction method to improve the image quality of CT image data, and noise reduction based on a statistical noise model and/or a scanner model). In addition, the X-ray CT apparatus 100 is capable of, for example, setting an imaging range in a main scan with higher accuracy, by acquiring a positioning image in a three-dimensional manner to acquire more information of the subject P.

As an example, the control function 135a extracts anatomical landmarks from the volume data acquired by a positional scan. Thereafter, the control function 135a compares positions of the extracted landmarks with model data in which positions of anatomical landmarks are defined, to acquire positions information of the regions of the subject P, such as the body trunk and the head. The control function 135a sets the imaging range in the main scan, on the basis of the positional information of each of the regions of the subject P. Specifically, the control function 135a is capable of automatically executing an imaging plan in a main scan, on the basis of a positioning scan. In this manner, the control function 135a is enabled to omit the time required for the operator's executing an imaging plan, and shorten the time to change from the positioning scan to the main scan.

Thereafter, the control function 135a performs a main scan. A main scan performed after execution of the first scan is an example of a second scan. For example, the control function 135a performs a main scan by a helical scan to scan the subject P in a helical manner, in the imaging range set on the basis of the positioning image. As illustrated in FIG. 3, because the rotor of the gantry 110 is rotated at the stage of the positioning scan, the control function 135a continuously rotates the rotor to perform the main scan.

However, generally, the rotational speed of the rotor in a positioning scan is different from the rotational speed of the rotor in a main scan. For example, when the rotational speed of the rotor in a positioning scan is higher than the rotational speed of the rotor in a main scan, rotation of the rotor is to be decelerated to perform a main scan, after the positioning scan is finished. A main scan is not started until rotation of the rotor reaches the setting value.

For example, an imaging plan of a main scan can be automatically executed by extracting anatomical landmarks from volume data acquired by the positional scan. This structure shortens the time required for an imaging plan of a main scan, in comparison with the case where the operator executes an imaging plan. However, even when the time required for an imaging plan is shortened, start of a main scan is delayed, when waiting time for acceleration or deceleration of the rotor occurs.

Figure 4:
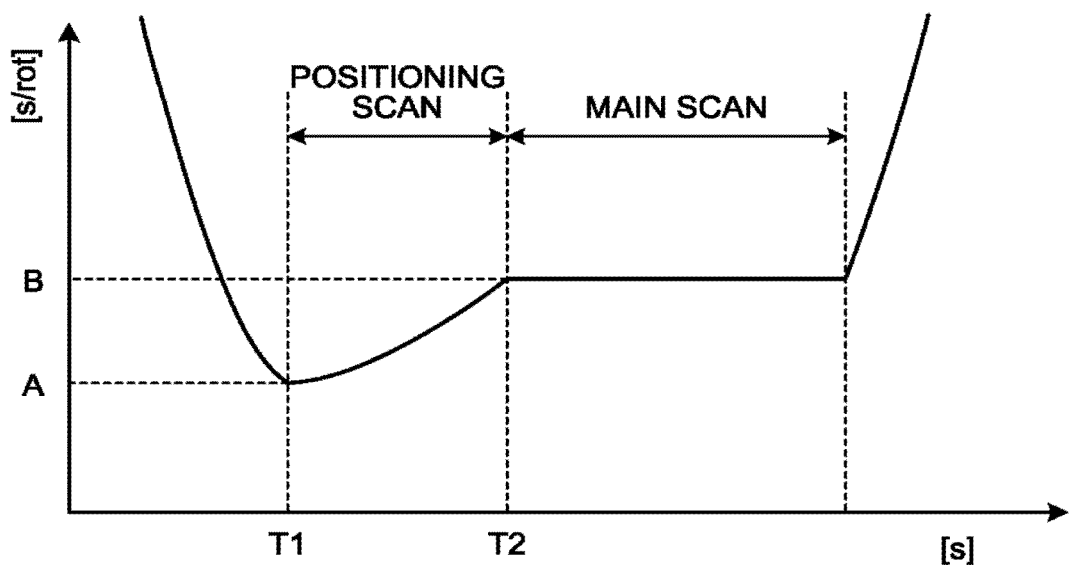
FIG. 4 is a diagram for explaining rotation of a rotor during a positioning scan according to the first embodiment.

For this reason, the control function 135a controls rotation of the rotor during a positioning scan such that the rotational speed of the rotor at the time when the positioning scan with the rotor rotated is finished is brought close to the rotational speed to start a main scan, to shorten the waiting time from the end of the positioning scan to start of the main scan. The following is a detailed explanation of shortening of the waiting time with the control function 135a, with reference to FIG. 4. FIG. 4 is a diagram for explaining rotation of the rotor during a positioning scan according to the first embodiment.

The horizontal axis in FIG. 4 indicates the time "s", and the vertical axis indicates the value "s/rot". The value "s/rot" is a reciprocal number of the number of rotations (rotational speed) of the rotor per unit time. Specifically, the value "s/rot" illustrated in FIG. 4 is a value indirectly indicating the rotational speed. The control function 135a is capable of controlling rotation of the rotor using the rotational speed, and also capable of controlling rotation of the rotor using the value indirectly indicating the rotational speed. In the following explanation, the rotational speed or the value indirectly indicating the rotational speed is also referred to as value related to the rotational speed. The value "s-rot" illustrated in FIG. 4 is an example of the value related to the rotational speed, and means the number of seconds required for a rotation of the rotor. For example, the value "s/rot" with a larger value indicates slower rotation, and the value "s/rot" is an infinite value when the rotor of the gantry 110 is in a stopped state.

In addition, as an example, the following explanation illustrates the case where a setting value "A" is set as a setting value related to the rotational speed of the rotor in a position scan, and a setting value "B" is set as a setting value related to the rotational speed of the rotor in a main scan, by selection of the expert plan or the like. Specifically, although the setting values related to the rotational speeds of the positioning scan and the main scan are any desired values, the following explanation illustrates the case where the setting value "A" set for the positioning scan is higher than the setting value "B" set for the main scan.

First, as illustrated in FIG. 4, the control function 135a accelerates rotation of the rotor in a stopped state to the setting value "A", and starts a positioning scan. The start time of the positioning scan is referred to as "T1" hereinafter. In this state, the control function 135a performs control to decelerate rotation of the rotor during the positioning scan to the setting value "B". For example, as illustrated in FIG. 4, the control function 135a performs control to gradually decelerate the rotational speed during the positioning scan such that the value related to the rotational speed of the rotor at the time when the positioning scan is finished becomes the setting value "B".

In the following explanation, the rotational speed of the rotor at the time when the positioning scan is finished is also referred to as first rotational speed. In the following explanation, the rotational speed (rotational speed corresponding to the setting value "B") of the rotor in the main scan is also referred to as second rotational speed. In the following explanation, the rotational speed (rotational speed corresponding to the setting value "A") of the rotor in the positioning scan is also referred to as third rotational speed. In FIG. 4, the control function 135a starts a positioning scan with the setting value "A" related to the third rotational speed, and controls rotation of the rotor during the positioning scan such that the value related to the first rotational speed becomes the setting value "B" related to the second rotational speed.

The following is an explanation of the case where the setting value "A" is "0.2 (s/rot)" and the setting value "B" is "0.35 (s/rot)", with respect to control of rotation during a positioning scan with the control function 135a, as an example. First, the control function 135a calculates the total number of rotations (for example, "20" rotations) of the rotor during the positional scan, on the basis of the imaging range and/or the slice thickness and the like determined by selection of the expert plan.

Thereafter, the control function 135a calculates a value "0.0075" obtained by dividing a difference "0.15 (s/rot)" between "0.2 (s/rot)" and "0.35 (s/rot)" by the calculated total number of rotations "20". The calculated value "0.0075" indicates a change quantity for each rotation of the number of seconds required for one rotation of the rotor. The control function 135a increases (decreases) the value "s/rot" related to the rotational speed of the rotor by "0.0075" for each rotation, to control rotation of the rotor during the positioning scan such that the positioning scan started at "0.2 (s/rot)" is finished at "0.35 (s/rot)".

In addition, the control function 135a controls the relative movement speed (couch speed) of the gantry 110 and the tabletop 122 during the positioning scan, in accordance with the rotational speed during the positioning scan. For example, the control function 135a controls the couch speed such that the number of views (View/cm) per unit length in the body axis direction of the subject P is fixed. The number of views indicates the number in a direction in which CT projection data is acquired.

As an example, in the case where the number of views obtained during one rotation of the rotor is "1080 (View/rot)", the number related to the rotational speed is "0.2 (s/rot)", and the couch speed is "1 (cm/s)", the number of views per unit length is "5400 (View/cm)". To decelerate the rotational speed to "0.25 (rot/s)" while the number of views per unit length is maintained at "5400 (View/cm)", the control function 135a performs control such that the couch speed becomes "0.8 (cm/s)". The control function 135a may control the couch speed, or may control the value (such as a reciprocal number of the couch speed) indirectly indicating the couch speed. In the following explanation, the couch speed or the value indirectly indicating the couch speed is also referred to as a value related to the relative movement speed of the gantry 110 and the tabletop 122.

The control function 135a also controls the tube current value used for generation of X-rays with the X-ray generator during a positioning scan, in accordance with rotation of the rotor during the positioning scan. For example, the control function 135a controls the tube current value in the X-ray generator 112 such that the value "mAs" serving as the product of the tube current value "mA" and the exposure time "s" is fixed. The value "mAs" is an index of high image quality. For example, the control function 135a increases the tube current value in accordance with acceleration of rotation of the rotor during the positioning scan, and decreases the tube current value in accordance with deceleration of rotation of the rotor.

For example, the control function 135a controls the tube current value "mA" to be inversely proportional to the value "s/rot" related to the rotational speed, to perform control to fix the value "mAs". As an example, in the case where the tube current value is "30 mA" when the value related to the rotational speed is "0.5 (s/rot)", the control function 135a performs control such that the tube current value becomes "20 mA" when the value related to the rotational speed is decelerated to "0.75 (s/rot)", and performs control such that the tube current value becomes "10 mA" when the value related to the rotational speed is decelerated to "1.5 (s/rot)".

Figure 5A:
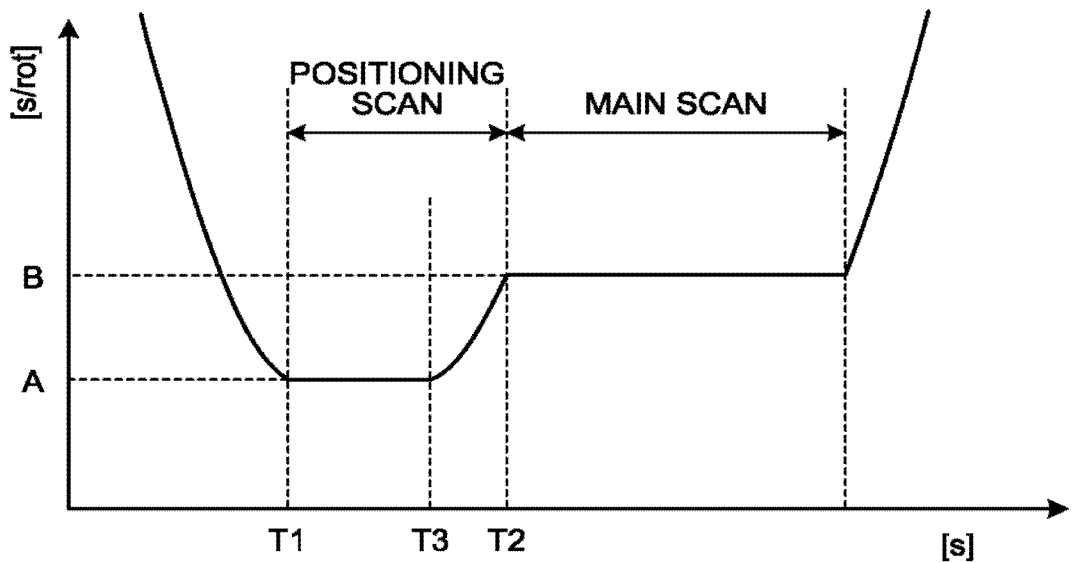
FIG. 5A is a diagram for explaining rotation of the rotor during a positioning scan according to the first embodiment.
Figure 5B:
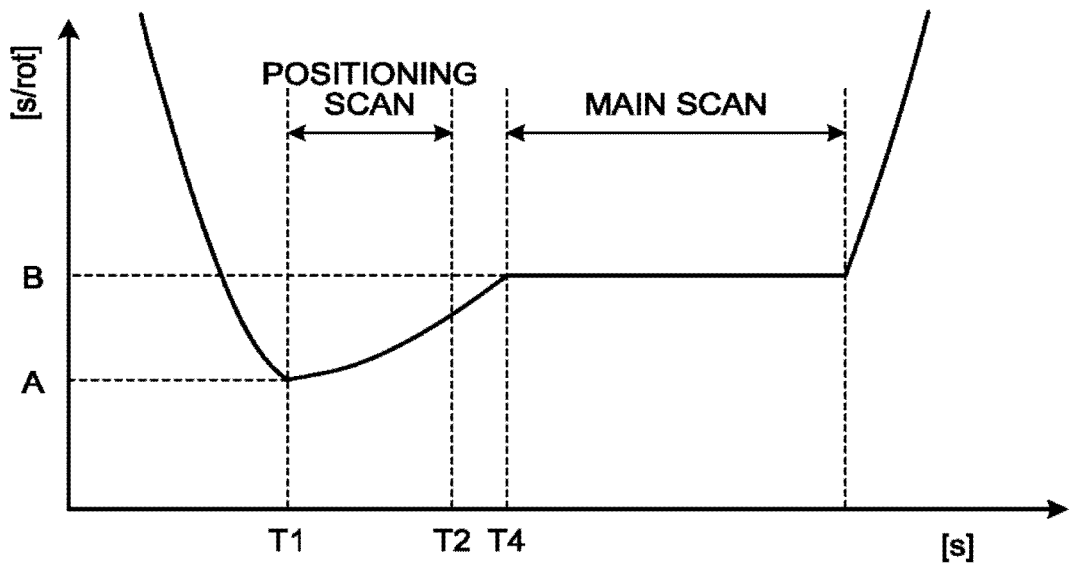
FIG. 5B is a diagram for explaining rotation of the rotor during a positioning scan according to the first embodiment.

The following is an explanation of another example of control of rotation of the rotor during a positional scan with the control function 135a, with reference to FIG. 5A and FIG. 5B. FIG. 5A and FIG. 5B are diagrams for explaining rotation of the rotor during a positional scan according to the first embodiment.

FIG. 4 illustrates the case where rotation of the rotor is kept decelerated from start to end of a positioning scan, but the control function 135a may change the rotational speed in only part of a period during the positioning scan. For example, as illustrated in FIG. 5A, the control function 135a performs control such that the value related to the rotational speed becomes the setting value "A" from time "T1" being the start time of the positioning scan to time "T3". Specifically, the control function 135a performs control such that the rotor rotates at fixed speed from the time "T1" to the time "T3".

The time "T3" is time determined on the basis of the time required for decelerating the value from the setting value "A" to the setting value "B" by the maximum acceleration of the rotor permitted with the gantry 110, and the time "T2" at which the positioning scan is finished. By controlling the value related to the rotational speed during the positioning scan as illustrated in FIG. 5A, the time required for deceleration can be reduced to the shortest time, while a more range in the subject P is scanned with rotation at fixed speed in the setting value "A" related to the rotational speed of the positioning scan.

In addition, FIG. 4 illustrates the case of performing control such that the value related to the rotational speed at the time when the positioning scan is finished agrees with the setting value "B" related to the rotational speed of the main scan. However, under some conditions, such as the length of the scan time of the positioning scan, the maximum acceleration permitted with the rotor, and a size of a difference between the setting value "A" and the setting value "B", it is supposed that, in some cases, the rotational speed does not become the setting value "B" at the time "T2" at which the positioning scan is finished, as illustrated in FIG. 5B.

In such cases, although the waiting time from the time "T2" at which the positioning scan is finished to time "T4" at which the main scan is started occurs, the control function 135a is capable of shortening the waiting time lasting until the start of the main scan, in comparison with the case where the whole positioning scan is performed with the setting value "A" (that is, the case where the positioning scan is finished with the setting value "A"). Specifically, in FIG. 5B, the control function 135a starts the positioning scan with the setting value "A" related to the third rotational speed, and controls rotation of the rotor during the positioning scan such that the value related to the first rotational speed is brought close to the setting value "B" related to the second rotational speed.

FIG. 4, FIG. 5A, and FIG. 5B illustrate the case where the positioning scan is started with the setting value "A" related to the rotational speed of the rotor in the positioning scan, but the rotational speed at the time when the positioning scan is started is not limited to the setting value "A". For example, as illustrated in FIG. 5B, in the case where the scan time of the positioning scan is short and it is impossible to decelerate rotation of the rotor from the setting value "A" to the setting value "B" during the positioning scan, the control function 135a may start the positioning scan with a value (slower rotational speed) larger than the setting value "A". As another example, the control function 135a may start the positioning scan with a value (higher rotational speed) smaller than the setting value "A", and decelerate rotation during the positioning scan such that the average value of the value related to the rotational speed during the positioning scan becomes the setting value "A".

In addition, FIG. 4, FIG. 5A, and FIG. 5B illustrate the case where the setting value "A" related to the rotational speed of the rotor in the positioning scan is smaller (higher) than the setting value "B" related to the rotational speed of the rotor in the main scan, but the setting value "A" may be larger (slower) than the setting value "B". In such cases, the control function 135a controls rotation during the positioning scan to accelerate rotation, which is reverse to deceleration of rotation during the positioning scan as described above.

In addition, the control function 135a may control rotation of the rotor during the positioning scan, in consideration of the exposure dose during the positioning scan. For example, the control function 135a controls rotation during the positioning scan, on the basis of the fact that the exposure dose of the subject P can be reduced more with the larger scan speed (the shorter time of the positioning scan), and that the waiting time lasting until the main scan is started can be shortened more as rotation of the rotor at the time when the positioning scan is finished is closer to the setting value "B".

As an example, first, the control function 135a performs a positioning scan with rotation at fixed speed, with the setting value "A" of higher rotation, from the time "T1" at which the positioning scan is started to the time "T3", as illustrated in FIG. 5A. Thereafter, the control function 135a decelerates rotation of the rotor with the maximum acceleration permitted with the gantry 110, from the time "T3" to the time "T2", and finishes the positioning scan with the setting value "B". As described above, the control function 135a is capable of reducing the exposure dose of the subject P, while shortening the waiting time lasting until the main scan is started, by controlling rotation such that the scan speed during the positioning scan is increased, under the conditions enabling the positioning scan to be finished with the setting value "B".

After CT projection data is acquired by the positioning scan, the generation function 135c reconstructs CT image data using the CT projection data, and generates a positioning image from the reconstructed CT image data. The generation function 135c may thicken the image quality of the reconstructed CT image data. Specifically, reducing the thickness of a reconstructed image may cause streak artifact included in the reconstructed CT image data due to motion or the like. Increasing the thickness of the reconstructed image makes such artifact indistinguishable and inconspicuous in the positioning image.

In addition, the control function 135a sets the imaging range in the main scan, on the basis of the positioning image. For example, first, the preprocessing function 135b performs logarithm transformation and/or correction processing on the CT projection data acquired by the positioning scan described above, to generate corrected CT projection data. The generation function 135c also reconstructs CT image data using the corrected CT projection data, to generate a positioning image from the CT image data. The control function 135a sets the imaging range in the main scan, on the basis of the positioning image.

For example, the control function 135a displays the positioning image on the display 132, and receives an operation to determine the imaging range from the operator who has referred to the positioning image, to set the imaging range in the main scan. As another example, the control function 135a extracts anatomical landmarks from the volume data acquired by the positioning scan. Thereafter, the control function 135a compares the positions of the extracted anatomical landmarks with model data in which positions of anatomical landmarks are defined, to acquire positional information of each of the regions of the subject P, such as the body trunk and the head. In this manner, the control function 135a acquires positional information of the regions set as an imaging target in the main scan by selection of the expert plan or the like, from the volume data acquired by the positioning scan. The control function 135a sets the imaging range in the main scan, on the basis of the acquired positional information.

After the imaging range is set, the control function 135a performs the main scan. For example, as illustrated in FIG. 4, FIG. 5A, and FIG. 5B, the control function 135a performs the main scan with rotation at fixed speed, with the setting value "B" related to the rotational speed of the rotor in the main scan. As another example, the control function 135a may control rotation of the rotor in the main scan for each of the regions of the subject P.

For example, first, the memory 134 stores the setting values related to the rotational speed of the rotor in the main scan, in association with the regions of the subject P, such as "0.5 (s/rot)" for the main scan for the body trunk, and "0.75 (s/rot)" for the main scan for the head. Thereafter, the acquisition function 135d acquires positional information of each of the regions of the subject P, from the volume data acquired by the positioning scan. For example, the acquisition function 135d compares the positions of anatomical landmarks extracted from the volume data with model data in which positions of anatomical landmarks are defined, to acquire positional information of each of the regions of the subject P, such as the body trunk and the head.

Thereafter, the control function 135a performs the main scan, while controlling rotation of the rotor on the basis of the setting values for the respective regions stored in the memory 134 and the positional information of each of the regions. The control function 135a controls the value related to the movement speed and the tube current value in the main scan, in the same manner as control of the value related to the relative movement speed of the gantry 110 and the tabletop 122, and the tube current value used for generation of X-rays with the X-ray generator in the positioning scan.

After the main scan is finished, the control function 135a determines whether any second scan and/or subsequent scans (additional scan) exists. For example, when the second scan exists, the control function 135a sets scan conditions for the second scan, by, for example, receiving selection of the expert plan. When the second scan includes a positioning scan, the control function 135a performs control to accelerate or decelerate rotation of the rotor rotated at fixed speed with the setting value related to the rotational speed of the rotor in the first main scan to the setting value related to the rotational speed of the rotor in the second positioning scan.

In addition, the control function 135a performs control to decelerate rotation of the rotor during the second positioning scan such that rotation of the rotor at the time when the second positioning scan is finished is brought close to the setting value related to the rotational speed of the rotor in the second main scan. When the second scan includes no positioning scan, the control function 135a performs control to accelerate or decelerate the rotor rotated at fixed speed with the setting value for the first main scan to the setting value for the second main scan, or maintain the rotational speed.

The control function 135a is also capable of acquiring the rotational speed in the second positioning scan or main scan and subsequent scans, in accordance with the purpose of the inspection and the region. For example, the memory 134 stores setting values therein in advance, such as "0.35 (s/rot)" for the positioning scan, "0.5 (s/rot)" for the main scan for the body trunk, and "0.75 (s/rot)" for the main scan for the head. The control function 135a performs control to accelerate or decelerate rotation of the rotor rotated at fixed speed with the setting value for the first main scan, or maintain rotation, on the basis of the setting values for the respective regions of inspection and the purpose and the scan conditions for the second scan. When no additional scan exists, the control function 135a stops rotation of the rotor, and ends the processing.

The following is an explanation of an example of a process performed with the X-ray CT apparatus 100, with reference to FIG. 6. FIG. 6 is a flowchart for explaining a flow of the process of the X-ray CT apparatus 100 according to the first embodiment. Steps S103, S104, and S107 are steps corresponding to the control function 135a. Steps S105 and S106 are steps corresponding to the control function 135a, the preprocessing function 135b, and the generation function 135c.

First, the subject P (patient) enters the room (Step S101), patient positioning is performed (Step S102), and thereafter the processing circuitry 135 performs patient registration (Step S103). In addition, the processing circuitry 135 receives selection of the scan conditions (Step S104), by selection of the expert plan or the like.

Thereafter, the processing circuitry 135 performs a positioning scan while controlling rotation of the rotor, on the basis of the setting value related to the rotational speed of the rotor in the main scan, to generate a positioning image (Step S105).

Thereafter, the processing circuitry 135 sets the imaging range and the like on the basis of the positioning image acquired by the positioning scan, and thereafter performs a main scan, to generate an X-ray CT image (Step S106). The processing circuitry 135 determines whether any additional scan exists (Step S107). When any additional scan exists (Yes at Step S107), the processing circuitry 135 proceeds to Step S104 again. By contrast, when no additional scan exists (No at Step S107), the processing circuitry 135 ends the process.

As described above, according to the first embodiment, the gantry 110 includes the X-ray generator in the rotor. The control function 135a controls rotation of the rotor during the positioning scan such that the value related to the first rotational speed serving as the rotational speed of the rotor at the time when a positioning scan performed prior to a main scan is finished is brought close to the setting value related to the second rotational speed serving as the rotational speed of the rotor in the main scan. This structure enables the X-ray CT apparatus 100 according to the first embodiment to shorten the waiting time lasting until the start of the main scan after the positioning scan is finished.

In addition, according to the first embodiment, the control function 135a controls the value related to the relative movement speed of the gantry 110 and the tabletop 122 on which the subject P is placed during the positioning scan, in accordance with rotation of the rotor during the positional scan. This structure enables the X-ray CT apparatus 100 according to the first embodiment to maintain the number of views in each of the positions of the subject P, even when the rotational speed is changed during the positional scan.

In addition, according to the first embodiment, the control function 135a controls the tube current value used for generation of X-rays with the X-ray generator during the positioning scan, in accordance with rotation of the rotor during the positional scan. This structure enables the X-ray CT apparatus 100 according to the first embodiment to maintain "mAs" at a substantially fixed value even when the rotational speed is changed during the positional scan, and maintain the image quality in each of the positions of the subject P.

Besides, according to the first embodiment, the control function 135a shortens the waiting time lasting from finish of the positioning scan to start of the main scan, to improve efficiency of the flow of inspection including the positioning scan and the main scan, and improve the throughput.

The first embodiment described above illustrates the case of controlling rotation of the rotor during the positioning scan, to shorten the waiting time lasting until the main scan is started after the positioning scan is finished. By contrast, the second embodiment illustrates the case of shortening the waiting time lasting until the positioning scan is started, by further controlling rotation of the rotor before the positioning scan is started.

The X-ray CT apparatus 100 according to the second embodiment has a configuration similar to the X-ray CT apparatus 100 illustrated in FIG. 1, and they are different in part of the processing performed with the control function 135a. For this reason, elements having structures similar to those explained in the first embodiment are denoted by the same reference numerals as those in FIG. 1, and an explanation thereof will be omitted.

For example, the control function 135a starts rotation of the rotor of the gantry 110, when the subject P enters the inspection room (when the patient enters the room). The control function 135a may sense that the subject P enters the room with a sensor or the like, to start rotation of the rotor with the sensing used as a trigger, or may start rotation of the rotor on the basis of an input operation performed with the operator when the subject P enters the room.

As another example, the control function 135a starts rotation of the rotor of the gantry 110, when positioning of the subject P is performed (at the time of patient positioning). The time of patient positioning is, for example, the time when positioning is started (when the subject P is placed on the couch 120). For example, the control function 135a may sense that the subject P is placed on the couch 120 with a sensor or the like, to start rotation of the rotor with the sensing used as a trigger, or may start rotation of the rotor on the basis of an input operation performed with the operator when positioning is started. The time of patient positioning may be the time in the middle of performing positioning, or the time at which positioning is finished.

For example, the control function 135a starts rotation of the rotor of the gantry 110, when patient registration for the subject P is performed (at the time of patient registration), or when the scan conditions are selected (at the time of scan condition selection). For example, the control function 135a starts rotation of the rotor with a trigger. The trigger is, for example, reception of input of the name of the subject P or the like, or reception of an operation of selection of the expert plan, from the operator through the input interface 131. When the projector used for patient positioning is included in the rotor and rotated together with the X-ray generator, the control function 135a starts rotation of the rotor after patient positioning is finished (for example, at the time of patient registration or scan condition selection).

For example, the control function 135a accelerates rotation of the rotor to the setting value "A" related to the rotational speed of the rotor in the positioning scan. For example, the control function 135a controls the scan control circuitry 133, to control the operation of the frame controller 118 and accelerate rotation of the rotor. The setting value "A" may be a value related to the rotational speed set at the time of scan condition selection, or a fixed value used in a positioning scan. When rotation of the rotor is started before selection of the scan conditions (such as the time when the patient enters the room, the time of patient positioning, and the time of patient registration), the control function 135a accelerates rotation of the rotor toward the fixed value.

As described above, the control function 135a performs control to accelerate rotation of the rotor to the setting value related to the rotational speed of the rotor in the positioning scan, before the positioning scan is started. Thereafter, the control function 135a controls the scan control circuitry 133, to control the operations of the X-ray irradiation control circuitry 111, the frame controller 118, the data acquisition system 116, and the couch driver 121 and perform the positioning scan.

Figure 7:
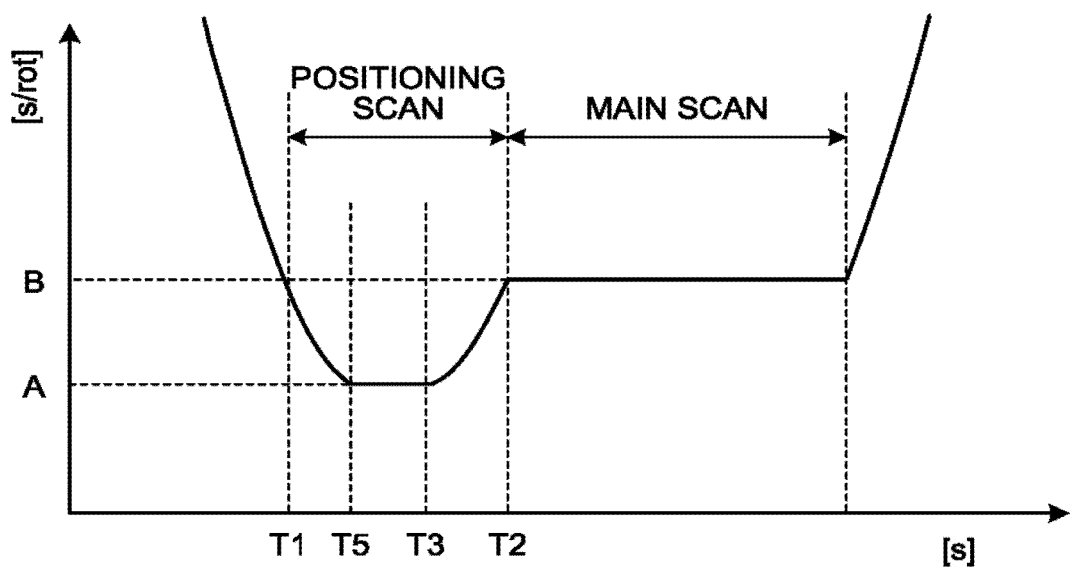
FIG. 7 is a diagram for explaining rotation of the rotor during a positioning scan according to a second embodiment.

The cases include the case where rotation of the rotor at the time when the control function 135a starts the positioning scan reaches the setting value "A", and the case where rotation does not reach the setting value "A". First, the following is an explanation of the case where rotation of the rotor at the time of start of the positioning scan does not reach the setting value "A", with reference to FIG. 7. FIG. 7 is a diagram for explaining rotation of the rotor during a positioning scan according to the second embodiment.

First, the control function 135a starts rotation of the rotor in a stopped state. The point in time at which rotation is started is the time before start of the positioning scan, such as the time when the patient enters the room, the time of patient positioning, the time of patient registration, and the time of scan condition selection. Thereafter, as illustrated in FIG. 7, the control function 135a starts a positioning scan (time "T1"), while reducing the value related to the rotational speed, without waiting until rotation of the rotor reaches the setting value "A". Specifically, the control function 135a starts the positioning scan while accelerating rotation of the rotor.

In addition, as illustrated in FIG. 7, the control function 135a accelerates rotation of the rotor to the setting value "A" (time "T5"). The control function 135a also maintains rotation of the rotor at the setting value "A", from the time "T5" to the time "T3". After the time "T3", the control function 135a increases (decelerates) rotation of the rotor to the setting value "B", and ends the positioning scan (time "T2"). The control function 135a may accelerate or decelerate rotation of the rotor to the setting value "B", after the positioning scan is started at the time "T1".

In addition, when rotation of the rotor at the time of start of the positioning scan has reached the setting value "A", the control function 135a maintains rotation of the rotor at the setting value "A", without decreasing (accelerating) the value related to the rotational speed after the positioning scan is started at the time "T1", and increases (decelerates) rotation of the rotor to the setting value "B" after the time "T3". As another example, the control function 135a increases (decelerates) the rotational speed to the setting value "B", after the positioning scan is started at the time "T1" with the setting value "A".

As described above, according to the second embodiment, the control function 135a performs control to accelerate rotation of the rotor to the setting value related to the third rotational speed serving as the rotational speed of the rotor in the positioning scan, before start of the positioning scan. This structure enables the X-ray CT apparatus 100 according to the second embodiment to shorten the waiting time before start of the positioning scan. For example, the X-ray CT apparatus 100 according to the second embodiment is enabled to promptly start a scan, without waiting until rotation of the rotor reaches the setting value, in an emergency.

In addition, according to the second embodiment, the control function 135a starts a positioning scan while accelerating the rotational speed. This structure enables the X-ray CT apparatus 100 according to the second embodiment to shorten the waiting time, even when rotation is started directly before the positioning scan and rotation at the time of start of the positioning scan does not reach the setting value.

The first and the second embodiments have been described above, but various different forms may be carried out other than the embodiments described above.

The embodiments described above illustrate the case of performing control such that rotation of the rotor during the positioning scan is accelerated or decelerated, but the control function 135a may neither accelerate nor decelerate rotation of the rotor during the positioning scan. For example, the control function 135a performs control such that rotation of the rotor during the positioning scan has a value related to the second rotational speed. Specifically, the control function 135a causes rotation of the rotor to reach the setting value "B" before the positioning scan is started, and controls rotation of the rotor such that the positioning scan and the main scan are performed with rotation at fixed speed with the setting value "B".

As an example, the control function 135a performs a positioning scan in the setting value "B" related to the rotational speed of the rotor in the main scan, without the setting value "A" related to the rotational speed of the rotor in the positioning scan. As another example, at the time of scan condition selection, the control function 135a sets scan conditions in which the setting value "A" related to the rotational speed of the rotor in the positioning scan is equal to the setting value "B" related to the rotational speed of the rotor in the main scan.

The control function 135a may perform acquisition in the positioning scan and the main scan at the same rotational speed, in consideration of the exposure dose in the positioning scan. For example, the control function 135a determines whether dose of X-rays irradiated to the subject P in the positioning scan is sufficiently reduced, on the basis of the basic property of the wedge 113 (bow-tie filter), and performs acquisition in the positioning scan and the main scan at the same rotational speed when the dose can be sufficiently reduced.

In addition, the embodiments described above illustrate the case where a positional scan is performed by a helical scan, but the positional scan may be performed by a non-helical scan.

The embodiments described above illustrate a positional scan performed while the rotor of the gantry 110 is rotated, as an example of the first scan. However, the embodiments are not limited thereto.

For example, the control function 135a performs a positioning scan, a first main scan performed after the positioning scan is performed, and a second main scan performed after the first main scan is performed.

In this case, first, the control function 135a controls rotation of the rotor during the positional scan such that the value related to the rotational speed of the rotor at the time when the positioning scan is finished is brought close to the setting value related to the rotational speed of the rotor in the first main scan. This structure enables the X-ray CT apparatus 100 to shorten the waiting time lasting until the main scan is started after the positioning scan is finished. The positioning scan is an example of the first scan. The first main scan is an example of the second scan.

In the case where the first main scan and the second main scan are performed, the control function 135a may perform no positioning scan.

Thereafter, the control function 135a controls rotation of the rotor during the first main scan such that the value related to the rotational speed of the rotor at the time when the first main scan is finished is brought close to the setting value related to the rotational speed of the rotor in the second main scan. This structure enables the X-ray CT apparatus 100 to shorten the waiting time lasting until the next main scan is started after the main scan is finished. The first main scan is an example of the first scan. The second main scan is an example of the second scan.

In the case where the first main scan and the second main scan are performed, the control function 135a may set the imaging range in the second main scan, on the basis of the X-ray CT image acquired by the first main scan. Specifically, the first scan may be a positioning scan, a main scan, or a positioning scan and a main scan.

The constituent elements in the apparatuses according to the first to the third embodiments are functional and conceptual ones, and are not always configured physically as illustrated. Specifically, the specific form of distribution and integration of each of the apparatuses is not limited to those illustrated, but the whole or part thereof may be configured to be functionally or physically distributed or integrated in desired unit, according to various loads and the situation of usage. In addition, the whole or desired part of each of the processing functions performed in the apparatuses may be achieved with a CPU and a computer program analyzed and executed in the CPU, or hardware by a wired logic.

In addition, the control method explained in the first to the third embodiments may be achieved by executing a control computer program prepared in advance with a computer, such as a personal computer and a work station. The control computer program can be distributed through a network, such as the Internet. The control computer program can also be recorded in a computer-readable recording medium, such as a hard disk, a flexible disk (FD), a CD-ROM, a MO, and a DVD, and executed by being read from the recording medium with a computer.

At least one of the embodiments described above shortens the waiting time in inspection including a plurality of scans.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   A gantry including an X-ray generator in a rotor; and
   processing circuitry configured to
   control rotation of the rotor during a first scan such that a value related to first rotational speed serving as rotational speed of the rotor at a time when the first scan is finished is brought close to a setting value related to second rotational speed serving as rotational speed of the rotor in a second scan, with respect to the first scan and the second scan performed after the first scan is performed,
   control to accelerate or decelerate rotation of the rotor during the first scan to the setting value related to the second rotational speed, and
   control a value related to relative movement speed of the gantry and a tabletop on which a subject is placed during the first scan, in accordance with rotation of the rotor during the first scan.

2. The X-ray CT apparatus according to claim 1, wherein the processing circuitry is configured to control to accelerate rotation of the rotor during the first scan to a setting value related to third rotational speed serving as rotational speed of the rotor in the first scan, and thereafter decelerate rotation to the setting value related to the second rotational speed.

3. The X-ray CT apparatus according to claim 2, wherein the processing circuitry is further configured to control a tube current value used for generation of X-rays with the X-ray generator during the first scan, in accordance with rotation of the rotor during the first scan.

4. The X-ray CT apparatus according to claim 3, wherein the processing circuitry is configured to control the X-ray generator to increase the tube current value in accordance with acceleration of rotation of the rotor during the first scan, and decrease the tube current value in accordance with deceleration of rotation of the rotor during the first scan.

5. The X-ray CT apparatus according to claim 1, wherein the processing circuitry is further configured to control a tube current value used for generation of X-rays with the X-ray generator during the first scan, in accordance with rotation of the rotor during the first scan.

6. The X-ray CT apparatus according to claim 5, wherein the processing circuitry is configured to control the X-ray generator to increase the tube current value in accordance with acceleration of rotation of the rotor during the first scan, and decrease the tube current value in accordance with deceleration of rotation of the rotor during the first scan.

7. The X-ray CT apparatus according to claim 5, wherein the processing circuitry is configured to control rotation of the rotor during the first scan such that the value related to the first rotational speed becomes the setting value related to the second rotational speed.

8. The X-ray CT apparatus according to claim 5, wherein the processing circuitry is further configured to control to accelerate rotation of the rotor to a setting value related to third rotational speed serving as rotational speed of the rotor in the first scan, before start of the first scan.

9. The X-ray CT apparatus according to claim 8, wherein the processing circuitry is configured to control to start acceleration of rotation of the rotor at a time when a patient enters a room, at a time of patient positioning, at a time of patient registration, or at a time of scan condition selection.

10. The X-ray CT apparatus according to claim 1, wherein the processing circuitry is configured to control rotation of the rotor during the first scan to the setting value related to the second rotational speed.

11. The X-ray CT apparatus according to claim 1, wherein the processing circuitry is configured to control rotation of the rotor during the first scan such that the value related to the first rotational speed becomes the setting value related to the second rotational speed.

12. The X-ray CT apparatus according to claim 1, wherein the processing circuitry is configured to control rotation of the rotor during the first scan such that the value related to the first rotational speed becomes the setting value related to the second rotational speed.

13. The X-ray CT apparatus according to claim 1, wherein the processing circuitry is further configured to control to accelerate rotation of the rotor to a setting value related to third rotational speed serving as rotational speed of the rotor in the first scan, before start of the first scan.

14. The X-ray CT apparatus according to claim 13, wherein the processing circuitry is configured to control to start acceleration of rotation of the rotor at a time when a patient enters the room, at a time of patient positioning, at a time of patient registration, or at a time of scan condition selection.

15. The X-ray CT apparatus according to claim 14, wherein the processing circuitry is configured to start the first scan while accelerating rotation of the rotor.

16. The X-ray CT apparatus according to claim 13, wherein the processing circuitry is configured to start the first scan while accelerating rotation of the rotor.

17. The X-ray CT apparatus according to claim 1, wherein the processing circuitry is further configured to control to accelerate rotation of the rotor to a setting value related to third rotational speed serving as rotational speed of the rotor in the first scan, before start of the first scan.

18. The X-ray CT apparatus according to claim 17, wherein the processing circuitry is configured to control to start acceleration of rotation of the rotor at a time when a patient enters a room, at a time of patient positioning, at a time of patient registration, or at a time of scan condition selection.

19. The X-ray CT apparatus according to claim 1, further comprising:
   a memory configured to store a setting value related to the rotational speed of the rotor in the second scan for each of regions of a subject, wherein
   the processing circuitry is configured to acquire positional information of each of the regions of the subject from a positioning image acquired by the first scan, and controls rotation of the rotor in the second scan, on the basis of the setting value and the positional information of each of the regions.

* * * * *